United States Patent [19]

Björkman

[11] Patent Number: 4,642,220
[45] Date of Patent: Feb. 10, 1987

[54] APPARATUS FOR CARRYING OUT ANALYSIS

[75] Inventor: Rune Björkman, Bälinge, Sweden

[73] Assignee: Pharmacia AB, Uppsala, Sweden

[21] Appl. No.: 723,750

[22] Filed: Apr. 16, 1985

Related U.S. Application Data

[63] Continuation of Ser. No. 448,910, Dec. 3, 1982, abandoned.

[30] Foreign Application Priority Data

Apr. 10, 1981 [SE] Sweden .................................. 8102316

[51] Int. Cl.[4] ............................................. B01L 11/00
[52] U.S. Cl. ....................................... 422/101; 422/70;
422/104; 422/71; 435/300; 435/809; 436/804;
436/809; 73/863.23
[58] Field of Search ............ 422/70, 71, 99, 100–102,
422/104; 436/804, 807–809; 435/293, 300, 301,
809, 810; 141/65, 115, 116; 73/863.23, 863.24,
863.32; 210/416.1, 927

[56] References Cited

U.S. PATENT DOCUMENTS

| | | | |
|---|---|---|---|
| 3,913,801 | 10/1975 | Wise et al. | 141/116 |
| 4,090,850 | 5/1978 | Chen et al. | 436/809 |
| 4,167,875 | 9/1979 | Meakin | 73/421 R |
| 4,427,415 | 1/1984 | Cleveland | 422/101 |
| 4,452,899 | 6/1984 | Alston | 422/100 |
| 4,461,328 | 7/1984 | Kenney | 422/100 |

OTHER PUBLICATIONS

Radio Immunoassay on Polycarbonate Membranes: A Sensitive and Simplified Method for the Detection and Quantitation of Antibody, R. Green et al, Applied Microbiolgy Mar. 1974, vol. 27, No. 3, pp. 475–479.
Immobilization of viral Antigens on Filter Paper for A[$^{125}$I] Staphylococcal Protein Aimmundassay: A Rapid and Sensitive Technique for Detection of Herpes Simplex Virus Antigens and Antiviral Antibodies, Journal of Immunological Methods, 29, (1979) pp. 369–386, Cleveland et al.

Primary Examiner—David L. Lacey
Attorney, Agent, or Firm—Fred Philpitt

[57] ABSTRACT

The invention relates to an apparatus for carrying out analyses comprising at least one incubation step and at least one separation step for separating a liquid phase from a phase, which is insoluble in said liquid phase. The apparatus comprises a plurality of reaction vessels (2), making it possible to simultaneously carry out similar working sequences with reaction mixtures in the separate reaction vessels, each of which has a porous bottom (3) connected to a separate chamber (8), the reaction vessels being able to retain the reaction mixture during the incubation steps. According to the invention, there is provided a pressure regulating system, which creates a higher relative pressure in the chambers (8) than in the reaction vessels (2). This pressure difference prevents leakage from the reaction vessels to the chambers.

3 Claims, 5 Drawing Figures

APPARATUS FOR CARRYING OUT ANALYSIS

This is a continuation of application Ser. No. 448,910, filed Dec. 3, 1982, now abandoned, and the benefits of 35 USC 120 are claimed relative to it.

This invention relates to an apparatus for carrying out analyses of the type including at least one incubation step and at least one separation step for separating a liquid phase from a phase, which is insoluble in said liquid phase, said apparatus comprising a plurality of reaction vessels making it possible to simultaneously carry out similar working sequences in the separate reaction vessels, each of which has a porous bottom element connected to separate chambers, the reaction vessels being able to retain a reaction mixture therein during the incubation step or steps.

Thus, such method of analysis always comprises at least one incubation step and at least one separation step, but it may also include a plurality of such steps. If necessary, the method may also include one or more washing steps. After a working sequence of such steps, a measurement is performed on either the insoluble or the liquid phase. Two sequences are said to be similar if their steps are equal or comparable with respect to duration, number and order.

Systems for carrying out this type of working sequences have been described by e.g. Green R L et al (Appl Microbiol (1974, p. 475-79), Cleveland P H et al (J Immunol Meth 29 (1975), p. 369-86), and in U.S. Pat. No. 4,090,850. All of these systems make use of different arrangements of a plurality of reaction vessels. The bottom of each vessel has one or more holes of such a size that a reaction mixture is retained in the vessel if the air pressures are equal on both sides of the bottom. The reaction vessels in any of these known systems are emptied simultaneously by suction, the insoluble phase being retained.

Specifically, Green R L et al use porous bottoms provided with filters and insoluble phases in the form of particles like bacteria or agarose. Cleaveland P H et al and U.S. Pat. No. 4,090,850 use bottoms with one hole and mention such insoluble phases as strips of paper, the walls of the reaction vessels or larger balls.

In all of these known systems there is a risk for;
1. Clogging of holes or filters
2. Leakage of liquid phase
3. Leakage of particles
4. Penetration of reaction mixtures into holes or filters
5. High non-specific adsorption (separation).

It is an object of this invention to provide an apparatus of the above type, in which there is no risk of leakage of liquids or particles during the incubation steps and in which detergents can be added for reducing non-specific adsorption. It is also an object of the invention to provide for many alternatives for selecting the insoluble phase and the porosity of the bottoms.

According to the invention these and other objects are achieved by means of an apparatus of the type indicated above. This apparatus is characterized by comprising an external pressure regulating system for creating a pressure differential between said chambers and reaction vessels such that leakage is prevented from the reaction vessels to the chambers during the incubation steps.

The enclosed drawings will in detail illustrate some specific embodiments of the invention.

Figure 1:
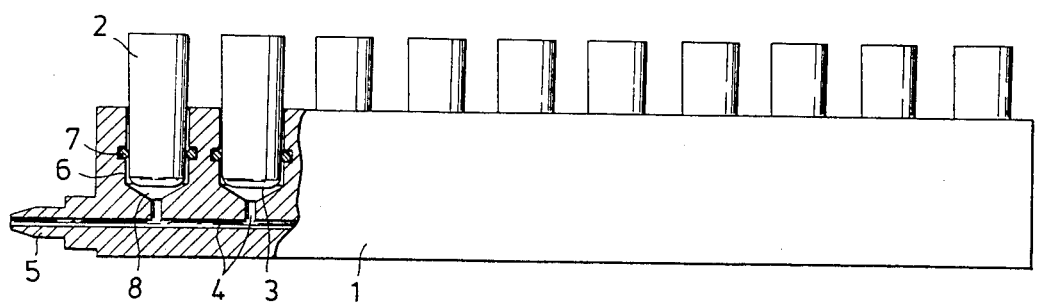
FIG. 1 is a side elevational view, partly in section, of a rack with reaction vessels according to the invention.

In FIG. 1 reference numeral 1 is a rack, which has a plurality of recesses 6, in which reaction vessels 2 are placed. The bottom elements 3 of the reaction vessels are porous. In the present specification and claims the term "porous bottom" means that there are pores extending between the upper and lower surfaces of the bottom element 3.

The rack 1 has, in its lower part, a channel 4, which has connections to each recess 6 and ends in a connecting nipple 5. O-rings 7 form a seal between the reaction vessels 2 and the recesses 6 when the reaction vessels 2 are placed in the rack. In this way there is formed a plurality of chambers 8, which upwards are delimited by the porous bottom elements 3. Downwards the chambers 8 are connected to the channel 4. By using the connecting nipple 5, the channel 4 may be connected to a pressure regulating system, e.g. to a suitable pump system for controlling the pressure of the chambers 8. The channel 4, the recesses 6, and the chambers 8 may take many different physical forms. FIG. 1 exemplifies a rack useful for measurement on a retained solid phase. When measurements are to be carried out on a liquid phase another type of rack should be used, e.g. a rack having larger chambers in which receptacles for the liquid phase can be placed. If necessary, a separated liquid phase is transferred to any suitable instrument for analysis.

Figure 2:
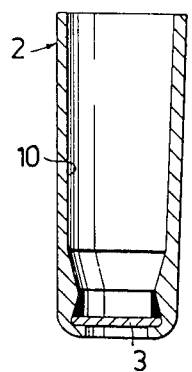
FIGS. 2 and 3 are sectional views of two alternative embodiments of reaction vessels for use in the device of FIG. 1.
Figure 3:
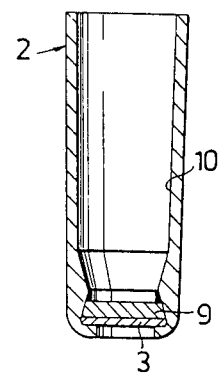

FIGS. 2 and 3 show two different types of reaction vessels, both of which have a porous bottom element 3. In addition thereto the vessel of FIG. 3 has a filter 9, which is applied to and covers the pores of the bottom element 3. For aqueous liquid phases the preferred filter is hydrophilic, particularly a three dimensional depth filter.

In an alternative embodiment the recesses 6 may serve as reaction vessels. In such an embodiment the recesses themselves are provided with porous bottoms, in the preferred embodiment combined with filters. The filters are selected as mentioned for the filter shown in FIG. 3.

The pore size of the porous bottom element 3 in FIG. 2 is of importance for the function of the invention. Pores which are too small may result in timeconsuming separations. If a particulate insoluble phase is unsuitably dimensioned, the pores may be clogged, making it impossible to perform separation steps. Pores which are too large do not retain particulate insoluble phases.

Increasing the pore size means that the difference between the highest and lowest allowable pressure difference decreases, i.e. there will be an increasing risk for leakage of air (gas) and reaction mixture respectively. In addition to being of a suitable pore-size, the bottom should have good mechanical strength and low non-specific adsorption for all chemicals involved in the analysis. We have found that hydrophobic membranes with pore sizes from about $1\mu$ to $20\mu$ are useful for the reaction vessels shown in FIG. 2, especially when biospecific reactions are involved. It is suitable to work with pressure differentials between 100 and 500 Pa when using these types of porous bottoms.

The preferred embodiment of the invention is represented in FIG. 3. In this Figure the bottom surface of the filter 9 is applied to the upper surface of the porous bottom element 3 and covers the pores thereof. The filter may be a three-dimensional depth filter. Such a filter is characterized by having a multitude of crossed fibers with capillaries being formed therebetween. These capillaries form a three-dimensional capillary network. If the depth filter is hydrophilic, e.g. made of cellulose or glass fibers, it will strongly retain hydrophilic liquids like water in its capillaries. This means that a high pressure differential can be applied between the chambers 8 and reaction vessels 2 before bubbling occurs. In most cases the bottom is broken before bubbling occurs. Preferably the pressure differential is higher than 200 Pa. The combination of the depth filter 9 and the porous bottom element makes it easier to select the proper pressure differential to prevent leakage of reaction mixture into the porous bottom element 3. A three-dimensional depth filter also has a high capacity of retaining an insoluble phase of particles without decreasing the flow rate during the separation steps. This is extremely important for certain small particulate phases, which form impermeable complexes with serum. Thus, there will be no clogging of the porous bottom element 3 if a three-dimensional depth filter, having capillaries catching the insoluble phase, is placed above and in contact with the bottom element, as shown in FIG. 3. If the bottom element 3 is hydrophobic, the pressure difference may be interrupted for shorter periods as e.g. during washing and addition of liquid reagents. We have used both hydrophobic bottom elements made of teflon and hydrophobized bottom elements of hydrophilic polymeric material. These types of bottom elements have been used for the vessel types shown in FIGS. 2 and 3.

Depth filters are commercially available, a suitable glass fibre type filter being Metrigrad ®, from Gelman Inc., Ann Harbour, USA.

In the preferred embodiment of FIG. 3 it is preferable to use a combination of a hydrophilic three-dimensional depth filter 9 and a hydrophobic or hydrophobized porous bottom element for reaction mixtures comprising a hydrophilic liquid phase like water.

Three important properties of the depth filter 9 are:

1. To prevent clogging of the porous bottom element 3

2. To have a high bubble point, i.e. allow application of a high pressure differential before bubbling occurs.

3. To retain a particulate insoluble phase with maintained high flow properties.

Three important properties of the porous bottom element 3 are;

1. To keep tight, when a pressure differential is applied.

2. To have high flow properties.

3. To keep tight without an applied pressure differential during shorter periods (e.g. during filling operations).

From the above it will be easy for a person of ordinary skill in this art to select the proper combinations of depth filter and porous bottom element.

For certain methods of analysis the inner wall 10 of the reaction vessel, the porous bottom 3 or the depth filter 9 may be used as the insoluble phase. Of course, such insoluble phases cannot clog the pores.

Figure 4:
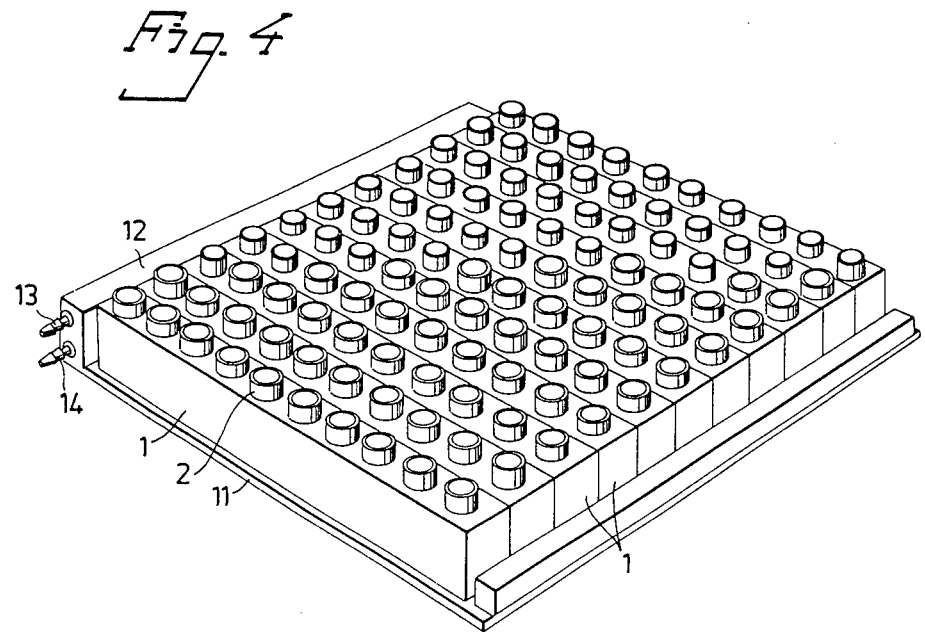
FIG. 4 is a perspective view of an analysis device made up of a plurality of racks according to FIG. 1.

FIG. 4 shows how a plurality of racks 1, carrying reaction vessels 2 are combined on a support plate 11. The connecting nipples 5 are sealingly connected to a common channel in an edge block 12 of a multi-rack module. This channel has two openings 13 and 14, each of which may be connected to a source of overpressure or reduced pressure contained in an external pressure regulating system. It is possible to arrange the reaction vessels and racks in almost any geometrical pattern. This is done by selecting different types of channels, racks and connections. If the channel in the edge of the multi-rack module is equipped with suitable valves, it is possible to use an optional number of racks 1. Of course, there are many ways to make the connections between the external pressure regulating system and the chambers 8 and/or the reaction vessels 2.

Figure 5:
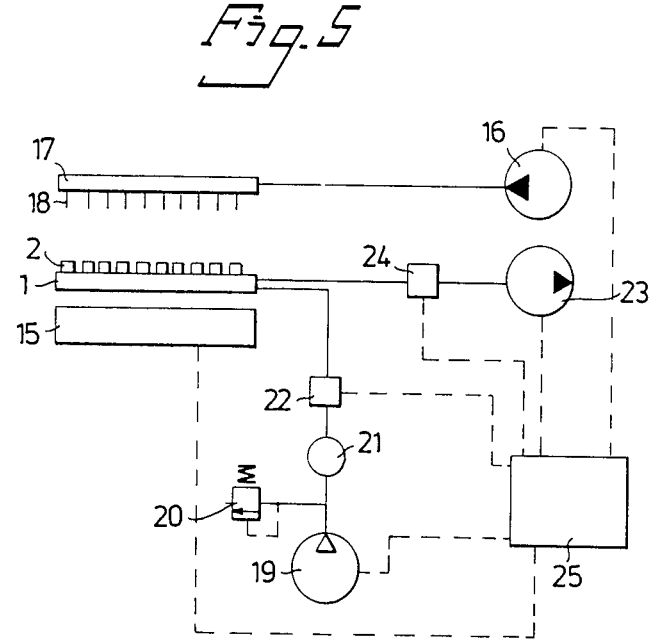
FIG. 5 is a schematic circuit diagram for an apparatus according to the invention.

FIG. 5 shows a rack 1 with reaction vessels 2 placed above a shaker 15 for stirring the reaction mixture. A dispensing pump 16 is connected to a dispenser 17. The dispenser 17 has a plurality of mouths 18, for delivering washing solution or components of the reaction mixture to the vessels 2 of the rack.

FIG. 5 also shows an external pressure regulating system connected to the channel 4 of the rack (compare FIG. 1). This pressure regulating system may comprise systems for applying overpressure and/or reduced pressure.

In FIG. 5 number 19 is a pump for applying overpressure, and the FIG. 5 also shows a pressure regulator 20, a flow indicator 21 and a valve 22. The pump 19 applies an overpressure in the channels 4 and chambers 8 relative to the pressure in the vessels 2 (FIG. 1). Leakage of the reaction mixture through porous bottom elements 3 is thereby prevented. The pressure regulator 20 is used to select the proper pressure and the valve 22 serves to connect or disconnect the pressure source. The flow indicator 21 indicates leakage of gas. The pressure system may be designed in many alternative ways. According to the invention the pump 19 may be replaced by any device reducing the pressure in the vessels 2 relative to that in the channel 4 or chambers 8. In FIG. 5 the system for reduced pressure is an evacuating pump 23 and a valve 24. The pump 23 (or any other device for reducing the pressure in the channels 4 or chambers 8 relative to the vessels 2) reduces the pressure in the channels 4 and chambers 8. Solutions contained in the vessels will thereby be drawn through the porous bottom elements 3 (FIG. 1). At the same time the insoluble phase is retained therein. The valve 24 is used to connect or disconnect the pump 23.

The pumps 16, 23 and 19 and the valves 22 and 24 are connected to an electronic or mechanical control unit 25, which may be programmed so that similar working sequences are carried out simultaneously.

The embodiments of the drawings show vessels 2 which are at ambient pressure. The chambers 8 are alternatingly connected to sources of overpressure or reduced pressure for incubation and separation, respectively. An alternative embodiment is the analogeous reversal, i.e. the chambers are at ambient pressure and the vessels 2 are alternatingly connected to sources of reduced pressure and overpressure for incubation and separation, respectively.

The apparatus according to the drawings operates in the following ways: The components of the reaction mixture may be added to the vessels 2 by means of the pump 16, or manually by pipettes. The pump 19 and the regulator 20 are used to select the proper pressure differential (counter pressure), which prevents leakage through the porous bottom elements 3. Bubbling occurs in the vessels 2 when the pressure is too high in the chambers 8, especially if they are designed according to FIG. 2. Bubbling is in many cases a drawback, but it may in others be a practical way for stirring. There is no leakage of gas (air) when the indicator 21 shows zero. During the incubation the shaker 15 may be started for stirring. After incubation the pump 19 is disconnected by closing the valve 22. At the same time the valve 24 is opened. This means that the pump 23 evacuates the chambers 8 whereby the liquid phase is drawn through the bottom element 3 leaving the insoluble phase in the vessels 2. Washing steps may be carried out in analogy with the incubation step.

Because of the pressure differential during the incubation steps the pressure in the chambers 8 is higher than that in the reaction vessels 2. In this specification and in the claims, pressure refers to forces mediated by gases. The invention operates in a similar way during the washing steps. The washing steps, however, are usually of shorter duration. In the preferred embodiment with a porous bottom combined with a depth filter it is possible to cancel the pressure differential during washing steps. This is preferably done if the reaction mixture has a hydrophilic liquid phase, e.g. water, and the reaction vessel used has a hydrophobic porous bottom combined with a hydrophilic depth filter.

During the separation steps the apparatus applies a reversed pressure differential, i.e. the pressure in the chambers will be lower than that in the reaction vessels 2. This means that the liquid phase will be drawn through the bottom, retaining the insoluble phase in the reaction vessels. The separation steps are mostly carried out very quickly, and therefore the pressure differential is usually much higher for a separation step compared to an incubation or washing step. The ordinary man skilled in the art realizes what combinations of steps the apparatus may carry out according to the invention.

Biospecific affinity reactions between a ligand and a receptor are involved in those analyses, which are preferred for the invention. Examples of such reactions are those between a lectin and carbohydrate, biotin and avidin, IgG and Protein A and, of course, immunological reactions between antigen or hapten and antibody. Another example is the reaction between an enzyme and its substrate for conversion of the substrate to a product. In all these methods either the ligand or the receptor may be bound to an analytically indicatable atom or group which e.g. may be radioactive, enzymatically active, fluorescent, luminescent or phosphorescent.

In the above preferred methods of analysis, the insoluble phase may be a solid phase of e.g. bacteria or water insoluble polymers such as crosslinked dextran, agarose, cellulose, starch, poly-(hydroxyalkylacrylate) or polyacrylamide and their derivatives. The physical form of the insoluble phase may be e.g. strips or discs of paper, balls, fibers, small particles and discs of membranes or filters. The inner walls of the vessels may also be used as the insoluble phase. A ligand or receptor is often separately bound to the insoluble phase before the analysis is carried out. The insoluble phase may be added or formed before or during the incubation steps. Examples of the latter are precipitation of an antigen-antibody-complex by adding antiserum against the antibody or addition of polyethylene glycol.

The above methods of analysis, in which one of the reactants is labelled, make use of a partition of the analytically indicatable atom or group between an insoluble phase and a liquid phase. It is important to point out that this partition should be uniquely related to the concentration of the substance to be determined.

The utility of this invention has been shown by comparative studies on commercially available methods of analysis. In all of these methods, biospecific affinity reactions were involved. We have compared the manufacturer's recommended methods for separation with the use of an apparatus according to this invention. The standard curves from the invention were as good as those emanating from the recommended separation methods. In these comparative studies insoluble phases in the form of particle and discs were used. All of these commercial methods comprised one or two incubation steps.

The advantage of the invention was the considerable saving of time while analysing a multitude of samples.

I claim:

1. Apparatus for carrying out analyses that comprise at least one incubation step and at least one step for separating a liquid hydrophilic phase from a phase which is insoluble in said liquid phase, said apparatus comprising
   (a) a plurality of reaction vessels which make it possible to simultaneously carry out similar working sequences in said reaction vessels,
   (b) a support structure including a plurality of recesses and supporting said plurality of reaction vessels in a desired array in said recesses,
   (c) a porous bottom element in a lower portion of each of said reaction vessels, each porous bottom element being able to retain a reaction mixture thereabove during an incubation step and defining a chamber in each of said recesses beneath said bottom elements,
   (d) a pressure regulating system connected to said chambers so as to create a desired pressure differential between said chambers and a space above the porous bottom element of each of said reaction vessels, said pressure regulating system including;
      (1) means to elevate the pressure in said chambers above the pressure within the reaction vessels so as to insure against liquid leakage from said reaction vessels into said chambers,
      (2) means to decrease the pressure in said chambers below the pressure within the reaction vessels so as to facilitate liquid flow downwardly through the porous bottom elements in said reaction vessels, and
      (3) means to control said pressure elevating means and said pressure decreasing means, respectively, and
   (e) a hydrophilic filter in the lower portion of each of said reaction vessels, each of said filters being fixedly applied against the upper surface of one of said porous bottom elements and covering the pores thereof, each of said filters being constructed so as to be penetrated by and to retain hydrophilic liquid, thereby permitting the application of a high pressure differential between said chambers and the interior of said reaction vessels by said pressure elevating means without bubbling occuring through said porous bottom elements.

2. An apparatus according to claim 1 wherein each of said porous bottom elements is constructed out of a hydrophobic material.

3. An apparatus according to claim 1 wherein each of said hydrophilic filters is a depth filter.

* * * * *